(12) United States Patent
Biggadike et al.

(10) Patent No.: US 7,538,127 B2
(45) Date of Patent: May 26, 2009

(54) MEDICINAL COMPOUNDS

(75) Inventors: Keith Biggadike, Stevenage (GB);
Philip Charles Box, Stevenage (GB);
Diane Mary Coe, Stevenage (GB);
Duncan Stuart Holmes, Stevenage (GB); Brian Edgar Looker, Stevenage (GB); Panayiotis Alexandrou Procopiou, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 569 days.

(21) Appl. No.: 10/544,869

(22) PCT Filed: Feb. 12, 2004

(86) PCT No.: PCT/EP2004/001415

§ 371 (c)(1),
(2), (4) Date: Aug. 8, 2005

(87) PCT Pub. No.: WO2004/071388

PCT Pub. Date: Aug. 26, 2004

(65) Prior Publication Data
US 2006/0148771 A1    Jul. 6, 2006

(30) Foreign Application Priority Data
Feb. 14, 2003  (GB) ................ 0303396.6

(51) Int. Cl.
*C07D 213/65* (2006.01)
*C07C 217/08* (2006.01)
*A61K 31/44* (2006.01)
*A61K 31/18* (2006.01)

(52) U.S. Cl. .............. 514/357; 514/378; 514/460; 514/646; 546/339; 548/240; 549/427; 564/299

(58) Field of Classification Search ............ None
See application file for complete search history.

(56) References Cited

U.S. PATENT DOCUMENTS
2,140,800 A    12/1938   Leemans (Continued)

FOREIGN PATENT DOCUMENTS
DE        3513885      10/1985

(Continued)

OTHER PUBLICATIONS

West, Anthony R., Solid State Chemistry and its Applications, Wiley, New York, 1988, pp. 358 & 365.*
Fuji et al., "Novel phosphodiesterase 4 inhibitor T-440 reverses and prevents human bronchial contraction induced by allergen," *J Pharmacol Exp Ther* 284(1):162 (1998).

Landells et al., "Oral administration of the phosphodiesterase (PDE)4 inhibitor, V11294A inhibits ex-vivo agonist-induced-cell activation," *Eur Resp J (/annu Cong Eur Resp Soc*, Geneva) 12(Suppl. 28) Abst P2393 (Sep. 1998).
Dr. Meyer Magarici; Riesgossobre broncodilatadores; SVMS; Nov. 29, 2005.

(Continued)

*Primary Examiner*—Zinna N Davis
(74) *Attorney, Agent, or Firm*—Robert J. Smith

(57) ABSTRACT

A compound of formula (I) or a salt, solvate, or physiologically functional derivative thereof, wherein: m is an integer of from 2 to 8; n is an integer of from 2 to 5; with the proviso that m+n is 4 to 10; $R^4$ and $R^5$ are independently selected from hydrogen and $C_{1-4}$alkyl with the proviso that the total number of carbon atoms in $R^4$ and $R^5$ not more than 4; $R^6$ and $R^7$ are independently selected from hydrogen and $C_{1-4}$alkyl with the proviso that the total number of carbon atoms in $R^6$ and $R^7$ is not more than 4, and $Ar^1$ is a group selected from (a), (b), (c) and (d).

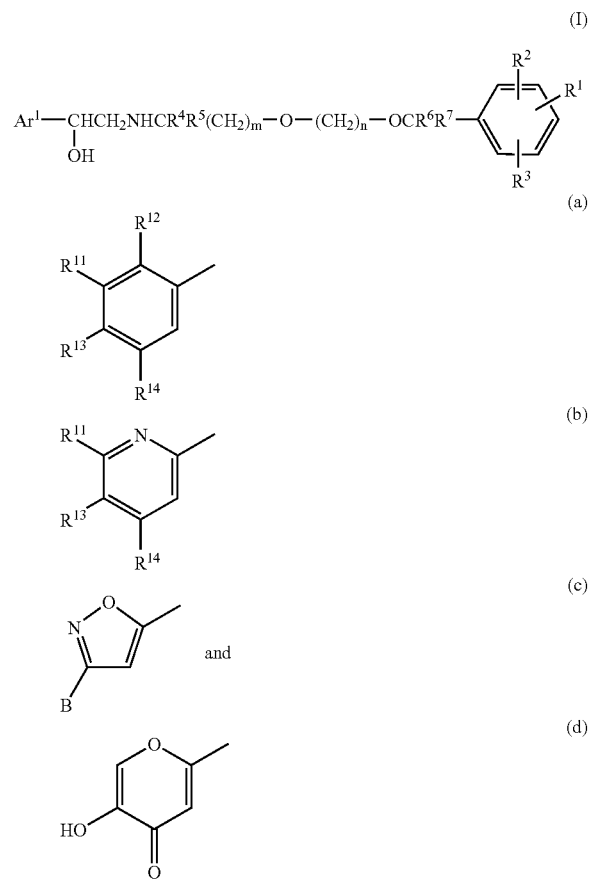

36 Claims, No Drawings

U.S. PATENT DOCUMENTS

| | | | |
|---|---|---|---|
| 2,918,408 | A | 12/1959 | Biel |
| 3,994,974 | A | 11/1976 | Murakami et al. |
| 4,730,008 | A | 3/1988 | Skidmore et al. |
| 4,778,054 | A | 10/1988 | Newell et al. |
| 4,811,731 | A | 3/1989 | Newell et al. |
| 4,853,381 | A | 8/1989 | Finch et al. |
| 4,853,382 | A | 8/1989 | Skidmore et al. |
| 4,908,386 | A | 3/1990 | Finch et al. |
| 4,937,268 | A | 6/1990 | Skidmore et al. |
| 4,963,564 | A | 10/1990 | Skidmore et al. |
| 4,990,505 | A | 2/1991 | Skidmore et al. |
| 4,992,474 | A | 2/1991 | Skidmore et al. |
| 4,997,986 | A | 3/1991 | Mitchell et al. |
| 5,035,237 | A | 7/1991 | Newell et al. |
| 5,066,678 | A | 11/1991 | Skidmore et al. |
| 5,091,422 | A | 2/1992 | Skidmore et al. |
| 5,099,068 | A | 3/1992 | Mitchell et al. |
| 5,109,023 | A | 4/1992 | Mitchell et al. |
| 5,126,375 | A | 6/1992 | Skidmore et al. |
| 5,225,445 | A | 7/1993 | Skidmore et al. |
| 5,243,076 | A | 9/1993 | Skidmore et al. |
| 5,283,262 | A | 2/1994 | Mitchell et al. |
| 5,290,815 | A | 3/1994 | Johnson et al. |
| 5,393,774 | A | 2/1995 | Pieper et al. |
| 5,552,438 | A | 9/1996 | Christensen, IV |
| 5,590,645 | A | 1/1997 | Davies et al. |
| 5,860,419 | A | 1/1999 | Davies et al. |
| 5,873,360 | A | 2/1999 | Davies et al. |
| 5,998,428 | A | 12/1999 | Barnette et al. |
| 6,321,747 | B1 | 11/2001 | Dmitrovic et al. |
| 6,632,666 | B2 | 10/2003 | Baust et al. |
| 7,135,600 | B2 | 11/2006 | Biggadike et al. |
| 7,361,787 | B2 * | 4/2008 | Box et al. ............... 564/38 |

FOREIGN PATENT DOCUMENTS

| | | |
|---|---|---|
| DE | 3524990 | 1/1986 |
| DE | 4028398 | 3/1992 |
| EP | 69715 | 1/1983 |
| EP | 162576 | 11/1985 |
| EP | 220054 | 4/1987 |
| EP | 220878 | 5/1987 |
| EP | 223410 | 5/1987 |
| EP | 286242 | 10/1988 |
| EP | 0286242 | 10/1988 |
| EP | 303465 | 2/1989 |
| EP | 0317206 | 5/1989 |
| EP | 0416951 | 3/1991 |
| EP | 223671 | 11/1991 |
| EP | 0401966 | 1/1994 |
| EP | 0947498 | 10/1999 |
| GB | 2064336 | 6/1981 |
| GB | 2129691 | 5/1984 |
| GB | 2140800 | 12/1984 |
| GB | 2159151 | 11/1985 |
| GB | 2162842 | 1/1986 |
| GB | 2165542 | 4/1986 |
| GB | 2169265 | 7/1986 |
| GB | 2176476 | 12/1986 |
| GB | 2178965 | 2/1987 |
| GB | 2230523 | 10/1990 |
| GB | 2242134 | 9/1991 |
| WO | 95/01170 | 1/1995 |
| WO | 95/19336 | 7/1995 |
| WO | WO 99/16766 | 4/1999 |
| WO | WO 99/47505 | 9/1999 |
| WO | WO 01/04118 | 1/2001 |
| WO | WO 01/13953 | 3/2001 |
| WO | WO 02/066422 | 8/2002 |
| WO | 00/51599 | 9/2002 |
| WO | WO 02/070490 | 9/2002 |
| WO | WO 02/076933 | 10/2002 |
| WO | WO 03/024439 | 3/2003 |
| WO | 2004/071388 | 8/2004 |

OTHER PUBLICATIONS

Drug Bank Chemical Compound Query Result Re Salmeterol; Jul. 31, 2000.

D. Iakovidis, et al. "Synthesis and beta-andrenoceptor agonist properties of (+/−)-1-(3',4'-dihydroxyphenoxy)-3-(3",4"-dimethooxyphenyl)ethylamino-2-propanol hydrochloride, (+/−)-(RO363.HCl, and the (2S)-(−)-isomer"; European Journal of Medicinal Chemistry; Jun. 6, 1999; vol. 34, No. 6, pp. 539-548.

Robert Hett, et al., "Enantionselective synthesis of salmeterol via asymmetric borane reduction"Tetrahedron Letters; 1994; vol. 35, No. 50.

U.S. Appl. No. 11/207,967, filed Aug. 19, 2005.
U.S. Appl. No. 11/207,967, final office action dated Jun. 19, 2007.
U.S. Appl. No. 11/426,657, non-final office dated Jun. 25, 2007.
U.S. Appl. No. 11/207,967, non-final office action dated Jan. 11, 2007.
U.S. Appl. No. 11/426,661, non-final office action dated Jan. 12, 2007.
U.S. Appl. No. 11/426,661, non-final office action dated Jul. 5, 2007.
U.S. Appl. No. 11/426,657, non-final office action dated Jan. 12, 2007.

Thomber "Isosterism and molecular modification in drug design" Chemical Society Reviews; 8(4) 563-580, no date provided.

U.S. Appl. No. 10/522,321, filed Jul. 6, 2005.
U.S. Appl. No. 11/207,667, filed Aug. 19, 2005.
U.S. Appl. No. 11/426,657, filed Jun. 27, 2006.
U.S. Appl. No. 11/426,661, filed Jun. 27, 2006.

Official Action, date mailed Mar. 15, 2007, U.S. Appl. No. 10/522,321.

McHale et al. "Expressin of human recombinant cAMP phosphodiesterase isozyme IV reverses growth arrest phenotypes in phosphodiesterase-deficient yeast" Mol. Pharmacol. 39:109-113.

Nicholson et al, "Differential modulation of tissue function and therapeutic potential of selective inhibitors of cyclic nucleotide phosphodiesterase isoenzymes." Trends Pharmacol Sci 12: 19-27(1991).

Torphy et al., "Role of cyclic nucleotide phosphodiesterase isozymes in intact canine trachealis", Mol. Pharmacol. 39:376-384 (1991).

* cited by examiner

MEDICINAL COMPOUNDS

CROSS-REFERENCE TO RELATED APPLICATIONS

This application is filed pursuant to 35 U.S.C. § 371 as a United States National Phase Application of International Application No. PCT/EP2004/001415 filed 12 Feb. 2004, which claims priority from GB 0303396.6 filed 14 Feb. 2003.

The present invention is concerned with phenethanolamine derivatives, processes for their preparation, compositions containing them and their use in medicine, particularly in the prophylaxis and treatment of respiratory diseases.

Certain phenethanolamine compounds are known in the art as having selective stimulant action at $\beta_2$-adrenoreceptors and therefore having utility in the treatment of bronchial asthma and related disorders. Thus GB 2 140 800 describes phenethanolamine compounds including 4-hydroxy-$\alpha^1$-[[[6-(4-phenylbutoxy)hexyl]amino]methyl]-1,3-benzene-dimethanol 1-hydroxy-2-naphthalenecarboxylate (salmeterol xinafoate) which is now used clinically in the treatment of such medical conditions.

Although salmeterol and the other commercially available $\beta_2$-adrenoreceptor agonists are effective bronchodilators, the maximum duration of action is 12 hours, hence twice daily dosing is often required. There is therefore a clinical need for compounds having potent and selective stimulant action at $\beta_2$-adrenoreceptors and having an advantageous profile of action.

According to the present invention, there is provided a compound of formula (I)

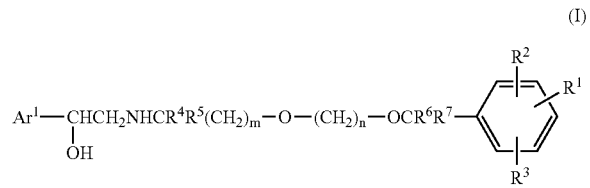

(I)

or a salt, solvate, or physiologically functional derivative thereof, wherein:

m is an integer of from 2 to 8;
n is an integer of from 2 to 5;
with the proviso that m+n is 4 to 10;
$R^1$ is selected from hydrogen, $C_{1-6}$alkyl, hydroxy, halo, $C_{1-6}$haloalkyl, —CN, —XC(O)NR$^9$R$^{10}$, —XNR$^8$C(O)R$^9$, —XNR$^8$C(O)NR$^9$R$^{10}$, —XNR$^8$SO$_2$R$^9$, —XSO$_2$NR$^9$R$^{10}$, XNR$^8$SO$_2$NR$^9$R$^{10}$, —XNR$^9$R$^{10}$, XN$^+$R$^8$R$^9$R$^{10}$, —XNR$^8$C(O)OR$^9$, —XCO$_2$R$^9$, —XNR$^8$C(O)NR$^8$C(O)NR$^9$R$^{10}$, —XSR$^9$, XSOR$^9$, and —XSO$_2$R$^9$;
or $R^1$ is selected from —X-aryl, —X-hetaryl, and —X-(aryloxy), each optionally substituted by 1 or 2 groups independently selected from hydroxy, $C_{1-6}$alkoxy, halo, $C_{1-6}$-alkyl, $C_{1-6}$haloalkyl, —NHC(O)($C_{1-6}$alkyl), —SO$_2$($C_{1-6}$alkyl), —SO$_2$(aryl), —SO$_2$NH$_2$, —SO$_2$NH($C_{1-6}$alkyl), —SO$_2$NH($C_{3-7}$cycloalkyl), —CO$_2$H, —CO$_2$($C_{1-6}$alkyl), —SO$_2$NH($C_{3-7}$cycloalkyl$C_{1-6}$alkyl), —NH$_2$, —NH($C_{1-6}$alkyl), or hetaryl optionally substituted by 1 or 2 groups independently selected from hydroxy, $C_{1-6}$alkoxy, halo, $C_{1-6}$alkyl, or $C_{1-6}$-haloalkyl;
X is —(CH$_2$)$_p$— or $C_{2-6}$ alkenylene;
p is an integer from 0 to 6, preferably 0 to 4;
$R^8$ and $R^9$ are independently selected from hydrogen, $C_{1-6}$alkyl, $C_{3-7}$-cycloalkyl, aryl, hetaryl, hetaryl($C_{1-6}$alkyl)- and aryl($C_{1-6}$alkyl)- and $R^8$ and $R^9$ are each independently optionally substituted by 1 or 2 groups independently selected from halo, $C_{1-6}$alkyl, $C_{1-6}$haloalkyl, —NHC(O)($C_{1-6}$alkyl), —SO$_2$($C_{1-6}$alkyl), —SO$_2$(aryl), —CO$_2$H, —CO$_2$($C_{1-4}$alkyl), —NH$_2$, —NH($C_{1-6}$alkyl), aryl($C_{1-6}$alkyl)-, aryl($C_{2-6}$alkenyl)-, aryl($C_{2-6}$alkynyl)-, hetaryl($C_{1-6}$alkyl)-, —NHSO$_2$aryl, —NH(hetarylC$_{1-6}$alkyl), —NHSO$_2$hetaryl, —NHSO$_2$($C_{1-6}$alkyl), —NHC(O)aryl, or —NHC(O)hetaryl:

or when $R^1$ is —XNR$^8$C(O)NR$^9$R$^{10}$, $R^8$ and $R^9$ may, together with the —NC(O)N— portion of the group $R^1$ to which they are bonded, form a saturated or unsaturated ring, preferably a 5-, 6-, or 7-membered ring, for example an imidazolidine or pyrimidine ring, such as imidazolidine-2,4-dione or pyrimidine-2,4-dione;

or where $R^1$ is —XNR$^8$C(O)OR$^9$, $R^8$ and $R^9$ may, together with the —NC(O)O— portion of the group $R^1$ to which they are bonded, form a saturated or unsaturated ring, preferably a 5-, 6-, or 7-membered ring, for example an oxazolidine ring, such as oxazolidine-2,4-dione;

$R^{10}$ is selected from hydrogen, $C_{1-6}$alkyl, $C_{3-7}$cycloalkyl, aryl, hetaryl, hetaryl($C_{1-8}$alkyl)- and aryl($C_{1-6}$alkyl)-, or $R^9$ and $R^{10}$, together with the nitrogen to which they are bonded, form a 5-, 6-, or 7-membered nitrogen containing ring;

and $R^9$ and $R^{10}$ are each optionally substituted by one or two groups independently selected from halo, $C_{1-6}$alkyl, and $C_{1-6}$-haloalkyl;

$R^2$ is selected from hydrogen, hydroxy, $C_{1-6}$alkyl, $C_{1-6}$alkoxy, halo, aryl, aryl($C_{1-6}$alkyl)-, $C_{1-6}$haloalkoxy, and $C_{1-6}$haloalkyl;

$R^3$ is selected from hydrogen, hydroxy, $C_{1-6}$alkyl, $C_{1-6}$alkoxy, halo, aryl, aryl($C_{1-6}$alkyl)-, $C_{1-6}$haloalkoxy, and $C_{1-6}$haloalkyl;

$R^4$ and $R^5$ are independently selected from hydrogen and $C_{1-4}$alkyl with the proviso that the total number of carbon atoms in $R^4$ and $R^5$ is not more than 4;

$R^6$ and $R^7$ are independently selected from hydrogen and $C_{1-4}$alkyl with the proviso that the total number of carbon atoms in $R^6$ and $R^7$ is not more than 4, and $Ar^1$ is a group selected from

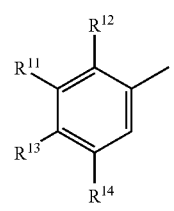

(a)

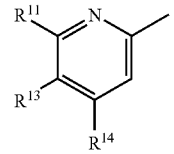

(b)

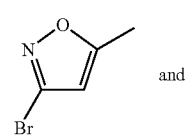

and (c)

-continued

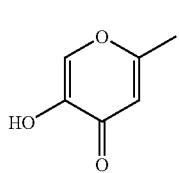

(d)

wherein $R^{11}$ represents hydrogen, halogen, —$(CH_2)_qOR^{15}$, —$NR^{15}C(O)R^{16}$, —$NR^{15}SO_2R^{16}$, —$SO_2NR^{15}R^{16}$, —$NR^{15}R^{16}$, —$OC(O)R^{17}$ or $OC(O)NR^{15}R^{16}$, and $R^{12}$ represents hydrogen, halogen or $C_{1-4}$alkyl;

or $R^{11}$ and $R^{12}$ together with the benzene ring atoms to which they are attached form a 5- or 6-membered heterocyclic ring;

$R^{13}$ represents hydrogen, halogen, —$OR^{15}$ or —$NR^{15}R^{16}$;

$R^{14}$ represents hydrogen, halogen, halo$C_{1-4}$alkyl, —$OR^{15}$, —$NR^{15}R^{16}$, —$OC(O)R^{17}$ or $OC(O)NR^{15}R^{16}$;

$R^{15}$ and $R^{16}$ each independently represents hydrogen or $C_{1-4}$alkyl, or in the groups —$NR^{15}R^{16}$, —$SO_2NR^{15}R^{16}$ and —$OC(O)NR^{15}R^{16}$, $R^{15}$ and $R^{16}$ independently represent hydrogen or $C_{1-4}$alkyl or together with the nitrogen atom to which they are attached form a 5-, 6- or 7-membered nitrogen-containing ring, $R^{17}$ represents an aryl (eg phenyl or naphthyl) group which may be unsubstituted or substituted by one or more substituents selected from halogen, $C_{1-4}$alkyl, hydroxy, $C_{1-4}$alkoxy or halo $C_{1-4}$alkyl; and q is zero or an integer from 1 to 4, provided that in the group (a) when $R^{11}$ represents —$(CH_2)_q OR^{15}$ and q is 1, $R^{13}$ is not OH.

In the compounds of formula (I) $R^1$ is suitably selected from hydrogen, $C_{1-6}$alkyl, hydroxy, halo, $C_{1-6}$haloalkyl, —$XNR^8(C)OR^9$, —$XNR^8C(O)NR^9R^{10}$, —$XNR^8SO_2R^9$, —$XSO_2NR^{11}R^{12}$, —$XNR^9R^{10}$, —$XNR^8C(O)OR^9$, $XSR^9$, $XSOR^9$, $XSO_2R^9$, or from X-aryl, X-hetaryl or X-aryloxy, optionally substituted as defined above.

X is suitably $(CH_2)_p$ wherein p is preferably zero.

$R^8$ and $R^{10}$ suitably represent hydrogen.

$R^9$ suitably represents hydrogen, $C_{1-6}$alkyl, $C_{3-7}$cycloalkyl, aryl, hetaryl or hetaryl($C_{1-6}$alkyl)-, any of which may be optionally substituted by $C_{1-6}$alkyl, $C_{1-6}$haloalkyl, —$SO_2(C_{1-6}$alkyl,), $NH_2$, aryl($C_{1-6}$alkyl), aryl($C_{2-6}$alkynyl), $NHSO_2$aryl, —NH(hetaryl($C_{1-6}$-alkyl), NHC(O)aryl or NHC(O)hetaryl.

In the definition of $R^1$, the term "5-, 6-, or 7-membered nitrogen containing ring" means a 5-, 6-, or 7-membered saturated or unsaturated ring which includes a nitrogen atom and optionally 1 or 2 other heteroatoms independently selected from nitrogen, sulphur, and oxygen. Suitable examples of such a ring include piperidinyl, morpholinyl, pyridyl, 2,4-dihydroxypyrimidinyl, and piperazinyl.

In the definition of $R^1$, the term "hetaryl" means a 5- to 10-membered heteroaromatic ring or bicyclic ring system which includes 1, 2, or 3 heteroatoms independently selected from oxygen, nitrogen and sulphur, such as thienyl, pyridyl, 2,4-dihydroxypyrimidinyl, 2,3-dihydroimidazo[2,1-b][1,3]thiazol-6-yl, or bipyridyl, preferably a 5- or 6-membered heteroaromatic ring.

As used herein, the term "aryl" either alone or in the term "aryloxy" means a monocyclic or bicyclic aromatic ring system, such as phenyl, naphthyl, or biphenyl. Preferably the term "aryl" means phenyl.

In the compounds of formula (I) the group $R^1$ is preferably selected from hydrogen, $C_{1-4}$alkyl, hydroxy, halo, —$NR^8C(O)NR^9R^{10}$, and —$NR^8SO_2R^9$ wherein $R^8$ and $R^9$ are as defined above or more suitably wherein $R^8$ is hydrogen and $R^9$ is selected from hydrogen, $C_{1-6}$alkyl, $C_{3-6}$cycloalkyl, and aryl and is optionally substituted as described above.

In the compounds of formulae (I) wherein the group $R^1$ is substituted by $R^8$ and/or $R^{10}$, $R^8$ and/or $R^{10}$ are suitably hydrogen.

In the compounds of formula (I), $R^2$ and $R^3$ are preferably independently selected from hydrogen, halogen (eg. fluorine or more preferably chlorine), halo $C_{1-6}$-alkyl (eg. $CF_3$), $C_{1-6}$alkyl (eg. methyl) and phenyl or substituted phenyl (eg. p-methoxyphenyl).

In the compounds of formula (I), $R^4$ and $R^5$ are preferably independently selected from hydrogen and methyl, more preferably $R^4$ and $R^5$ are both hydrogen.

In the compounds of formula (I) $R^6$ and $R^7$ are preferably independently selected from hydrogen and methyl, more preferably $R^6$ and $R^7$ are both hydrogen.

In the compounds of formula (I), m is suitably 4, 5 or 6, more suitably 4 or 5 and preferably 5 and n is suitably 2 or 3 and preferably n is 2.

In the compounds of formula (I) the group $R^1$ is preferably attached to the para- or meta-position, and more preferably to the meta-position relative to the —$OCR^6R^7$-link. The groups $R^2$ and $R^3$ are each independently preferably attached to the ortho- or meta-position, more preferably to the ortho position relative to the —$OCR^6R^7$-link.

In one preferred embodiment $R^1$ represents a substituent as defined above, other than hydrogen, most preferably attached to the meta-position relative to the —$OCR^6R^7$-link, and $R^2$ and $R^3$ each represent hydrogen.

In another preferred embodiment $R^1$ represents hydrogen and $R^2$ and $R^3$ each represent a substituent as defined above, at least one of which is other than hydrogen, and $R^2$ and $R^3$ are each independently attached to the ortho- or meta-positions relative to the —$OCR^6R^7$-link. In a particular embodiment, when $R^2$ and $R^3$ each represent halogen they are preferably attached at the ortho positions and when $R^2$ and $R^3$ each represent methyl they are preferably attached at the meta positions.

In the compounds of formula (I) the group $Ar^1$ is preferably selected from groups (a) and (b) above. In said groups (a) and (b), when $R^{11}$ represents halogen this is preferably chlorine or fluorine. $R^{15}$ and $R^{16}$ preferably each independently represent hydrogen or methyl. $R^{17}$ preferably represents substituted phenyl. The integer n preferably represents zero or 1.

Thus for example —$(CH_2)_nOR^{15}$ preferably represents —OH or —$CH_2OH$;

—$NR^{15}C(O)R^{16}$ preferably represents —NHC(O)H;

—$SO_2NR^{15}R^{16}$ preferably represents —$SO_2NH_2$ or —$SO_2NHCH_3$;

—$NR^{15}R^{16}$ preferably represents —$NH_2$;

—$OC(O)R^{17}$ preferably represents substituted benzoyloxy eg. —OC(O)—$C_6H_4$-(p-$CH_3$); and —$OC(O)N R^{15}R^{16}$ preferably represents —$OC(O)N(CH_3)_2$.

When $R^{11}$ together with $R^{12}$ forms a 5- or 6-membered heterocyclic ring this preferably contains at least one nitrogen atom and optionally one or more further heteroatoms selected from S and O. The heterocyclic ring may be optionally substituted by, for example =O, or —$COOR^{18}$, (where $R^{18}$ represents hydrogen or $C_{1-4}$alkyl), $C_{1-4}$alkyl or halo. The moiety —$R^{11}$—$R^{12}$— preferably represents a group:

—NH—CO—$R^{19}$ or —NH—$SO_2R^{19}$ where $R^{19}$ is an alkyl, alkenyl or alkyoxy group or moiety;

—NH—R²⁰— where R²⁰ is an alkyl or alkenyl group or moiety optionally substituted by COOR¹⁸; or
—NH—CO—S—.
Particularly preferred groups (a) and (b) may be selected from the following groups (i) to (xx):
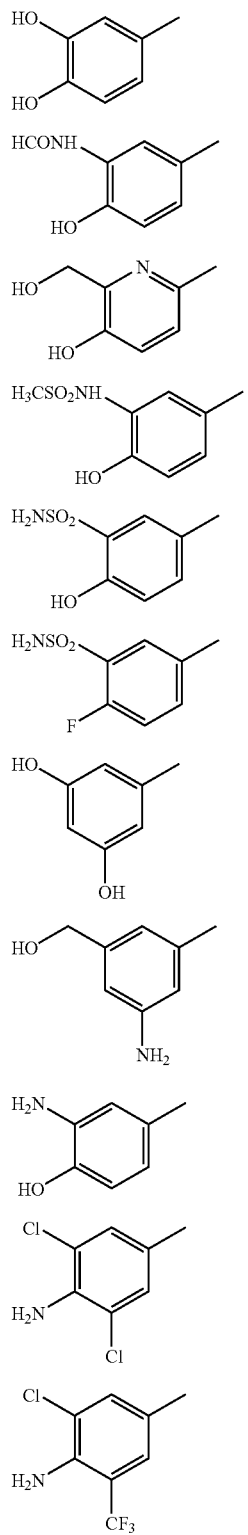
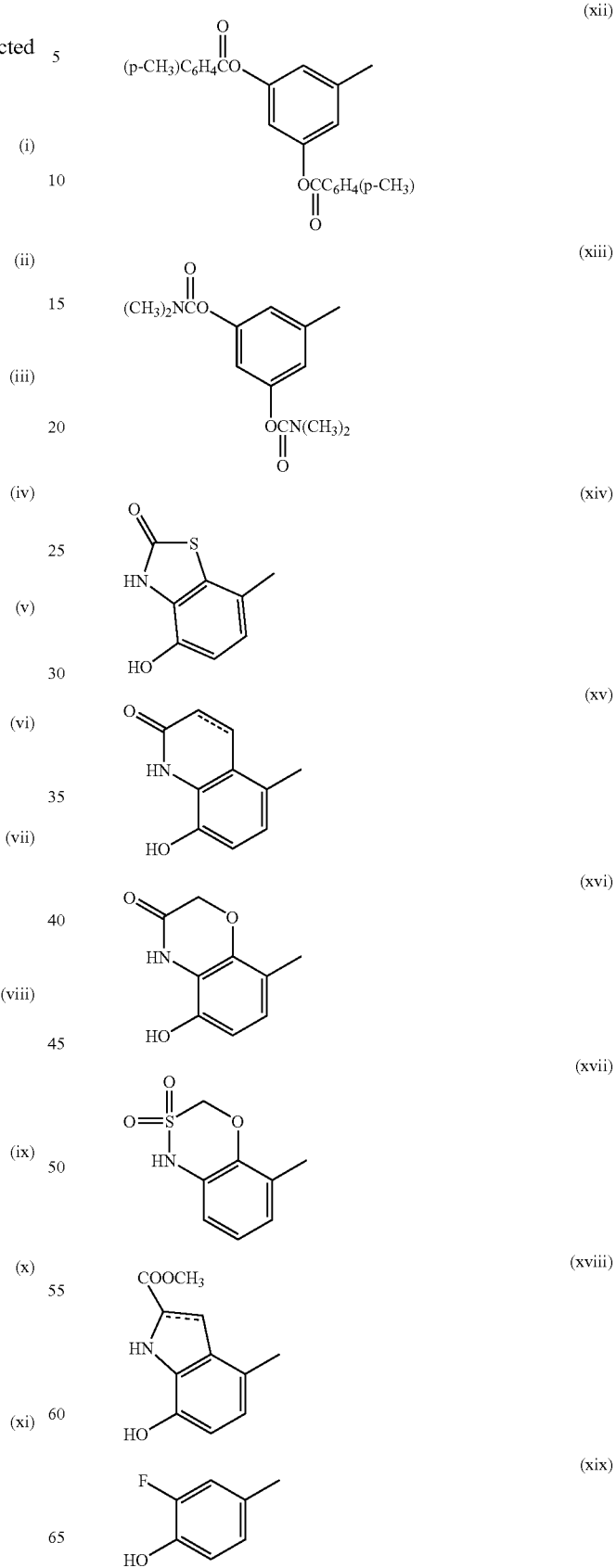

-continued

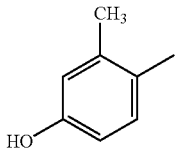
(xx)

wherein the dotted line in (xv) and (xviii) denotes an optional double bond. Particularly preferred groups $Ar^1$ include structures (ii) (iii) (iv) (x) and (xix).

It is to be understood that the present invention covers all combinations of particular and preferred groups described hereinabove.

The compounds of formula (I) include an asymmetric centre, namely the carbon atom of the

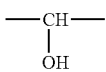

group. The present invention includes both (S) and (R) enantiomers either in substantially pure form or admixed in any proportions.

Similarly, where $R^4$ and $R^5$ are different groups or where $R^6$ and $R^7$ are different groups, the carbon atom to which they are attached is an asymmetric centre and the present invention includes both (S) and (R) isomers at these centres either in substantially pure form or admixed in any proportions.

Thus the compounds of formulae (I) include all enantiomers and diastereoisomers as well as mixtures thereof in any proportions.

Preferred compounds of the invention include:
(1R)-1-(4-amino-3,5-dichlorophenyl)-2-[(6-{2-[(2,6-dichlorobenzyl)oxy]ethoxy}hexyl)amino]ethanol;
6-{2-[(6-{2-[(2,6-dichlorobenzyl)oxy]ethoxy}hexyl)amino]-1-hydroxyethyl}$_2$-(hydroxymethyl)pyridin-3-ol;
4{(1R)-2-[(6-{2-[(2,6-dichlorobenzyl)oxy]ethoxy}hexyl)amino]-1-hydroxyethyl}-2-fluorophenol;
N-(5-{(1R)-2-[(6-{2-[(2,6-dichlorobenzyl)oxy]ethoxy}hexyl)amino]-1-hydroxyethyl}-2-hydroxyphenyl)methanesulfonamide; and
5-[(1R)-2-({6-[(2-{[(2,6-dichlorophenyl)methyl]oxy}ethyl)oxy]hexyl}amino)-1-hydroxyethyl]-2-hydroxyphenyl}formamide and salts, solvates and physiologically functional derivatives thereof.

Salts and solvates of compounds of formulae (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formulae (I) and (Ia) and their pharmaceutically acceptable salts, solvates, and physiologically functional derivatives.

By the term "physiologically functional derivative" is meant a chemical derivative of a compound of formula (I) having the same physiological function as the free compound of formula (I), for example, by being convertible in the body thereto. According to the present invention, examples of physiologically functional derivatives include esters.

Pharmaceutically acceptable esters of the compounds of formula (I) may have a hydroxyl group converted to a $C_{1-6}$alkyl, aryl, aryl $C_{1-6}$alkyl, or amino acid ester.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, phenylacetic, substituted phenyl acetic eg. methoxyphenyl acetic, sulphamic, sulphanilic, succinic, oxalic, fumaric, maleic, malic, glutamic, aspartic, oxaloacetic, methanesulphonic, ethanesulphonic, arylsulponic (for example p-toluenesulphonic, benzenesulphonic, naphthalenesulphonic or naphthalenedisulphonic), salicylic, glutaric, gluconic, tricarballylic, mandelic, cinnamic, substituted cinnamic (for example, methyl, methoxy, halo or phenyl substituted cinnamic, including 4-methyl and 4-methoxycinnamic acid and α-phenyl cinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, bezeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

As mentioned above, the compounds of formula (I) are selective $\beta_2$-adrenoreceptor agonists as demonstrated using functional or reporter gene readout from cell lines transfected with human beta-adrenoreceptors as described below. Compounds according to the present invention also have the potential to combine long duration of effect with rapid onset of action. Furthermore, certain compounds have shown a favourable therapeutic index in animal models. In addition, compounds of the invention demonstrate pharmacokinetic properties that have the potential to reduce systemic exposure to said compounds. As such, compounds of the invention may be suitable for once-daily administration.

Therefore, compounds of formulae (I) and their pharmaceutically acceptable salts, solvates, and physiologically functional derivatives have use in the prophylaxis and treatment of clinical conditions for which a selective $\beta_2$-adrenoreceptor agonist is indicated. Such conditions include diseases associated with reversible airways obstruction such as asthma, chronic obstructive pulmonary diseases (COPD) (e.g. chronic and wheezy bronchitis, emphysema), respiratory tract infection and upper respiratory tract disease (eg. rhinitis, including seasonal and allergic rhinitis).

Other conditions which may be treated include premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

Accordingly, the present invention provides a method for the prophylaxis or treatment of a clinical condition in a mammal, such as a human, for which a selective $\beta_2$-adrenoreceptor agonist is indicated, which comprises administration of a therapeutically effective amount of a compound of formula (I) or a pharmaceutically acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a compound of formula (I) or a pharmaceutically acceptable salt, solvate, or physiologically functional derivative thereof for use in medical therapy, particularly, for use in the prophylaxis or treatment of a clinical condition in a mammal, such as a human, for which a selective $\beta_2$-adrenoreceptor agonist is indicated. In particular, there is provided a compound of formula (I) or a pharmaceutically acceptable salt, solvate, or physiologically functional derivative thereof for the prophylaxis or treatment of a disease associated with reversible airways obstruction such as asthma, chronic obstructive pulmonary disease (COPD), respiratory tract infection or upper respiratory tract disease. In a further aspect, there is provided a compound of formula (I) or a pharmaceutically acceptable salt, solvate, or physiologically functional derivative thereof for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a compound of formula (I) or a pharmaceutically acceptable salt, solvate, or physiologically functional derivative thereof in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease. In a further aspect, there is provided a compound of formula (I) or a pharmaceutically acceptable salt, solvate, or physiologically functional derivative thereof in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a compound of formula (I) or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered by inhalation at a dose of from 0.0005 mg to 10 mg, preferably 0.005 mg to 0.5 mg, for example 0.05 mg to 0.5 mg. The dose range for adult humans is generally from 0.0005 mg to 10 mg per day and preferably 0.01 mg to 1 mg per day, most preferably 0.05 mg to 0.5 mg per day.

While it is possible for the compound of formula (I) or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I) or a pharmaceutically acceptable salt, solvate, or physiologically functional derivative thereof, and a pharmaceutically acceptable carrier or excipient, and optionally one or more other therapeutic ingredients.

The compounds and pharmaceutical formulations according to the invention may be used in combination with or include one or more other therapeutic agents, for example anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example, an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a corticosteroid, and/or an antcholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, and 6α,9α-difluoro-17α-[(2-furanylcarbonyl)oxy]-11β-hydroxy-16α-methyl-3-oxo-androsta-1,4-diene-17β-carbothioic acid S-fluoromethyl ester and 6α,9α-difluoro-11β-hydroxy-16α-methyl-17α-[(4-methyl-1,3-thiazole-5-carbonyl)oxy]-3-oxo-androsta-1,4-diene-17,β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g.

chemokine antagonists) or inhibitors of cytokine synthesis. Suitable other β$_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for an another description of said assay.

The preferred PDE4 inhibitors for use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]; these are examples of compounds which bind preferentially to the low affinity binding site and which have an $IC_{50}$ ratio of 0.1 or greater.

Other compounds of interest include:

Compounds set out in U.S. Pat. No. 5,552,438 issued 03 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms; AWD-12-281 from elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P 2393); roflumilast (CAS reference No 162401-32-3) and a pthalazinone (WO99/47505, the disclosure of which is hereby incorporated by reference) from Byk-Gulden; Pumafentrine, (−)-p-[(4aR*, 10 bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

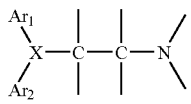

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chiropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Examples of preferred anti-histamines include methapyrilene and loratadine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a corticosteroid.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a corticosteroid.

The invention thus provides, in a further aspect, a combination comprising a compound of formula (I) a pharmaceutically acceptable salt, solvate or physiologically functional derivative thereof together with an anticholinergic and a PDE4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

Hereinafter, the term "active ingredient" means a compound of formula (I) or (Ia), or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration, although the most suitable route may depend upon, for example, the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di or poly-saccharides (eg. lactose or starch). Use of lactose is preferred.

Each capsule or cartridge may generally contain between 20 μg-10 mg of the compound of formula (I) optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134, U.S. Pat. Nos. 6,632,666, 5,860,419, 5,873,360 and 5,590,645 or Diskhaler, see GB 2178965, 2129691 and 2169265, U.S. Pat. Nos. 4,778,054, 4,811,731, 5,035,237, the disclosures of which are hereby incorporated by reference) or metered in use (eg as in Turbuhaler, see EP 69715 or in the devices described in U.S. Pat. No. 6,321,747 the disclosures of which are hereby incorporated by reference). An example of a unit-dose device is Rotahaler (see GB 2064336 and U.S. Pat. No. 4,353,656, the disclosures of which are hereby incorporated by reference). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulisation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

According to a further aspect of the invention, there is provided a process for preparing a compound of formula (I) or a salt, solvate, or physiologically functional derivative thereof which comprises a process as described below followed where necessary or desired by one or more of the following steps in any order:
(i) optional removal of any protecting groups;
(ii) optional separation of an enantiomer or diastereoisomer from a mixture of enantiomers or diastereoisomers;
(iii) optional conversion of the product to a corresponding salt, solvate, or physiologically functional derivative thereof.
(iv) optional conversion of a group $R^{1a}$, $R^{2a}$ and/or $R^{3a}$ to a group $R^1$, $R^2$ and/or
$R^3$ respectively.

In one general process (A), a compound of formula (I) may be obtained by deprotection of a protected intermediate, for example of formula (II):

$$Ar^{1a}-\underset{\underset{OP^2}{|}}{C}HCH_2NP^1CR^4R^5(CH_2)_m-O-(CH_2)_n-OCR^6R^7-\underset{R^{3a}}{\overset{R^{2a}}{\bigcirc}}R^{1a}$$

(II)

or a salt or solvate thereof, wherein $R^4$, $R^5$, $R^6$, $R^7$, m, and n are as defined for the compound of formula (I) or (Ia), and $R^{1a}$, $R^{2a}$, and $R^{3a}$ are each independently either the same as $R^1$, $R^2$, and $R^3$ respectively as defined for the compound of formulae (I) or (Ia) or a precursor for said group $R^1$, $R^2$, or $R^3$, Aria represents an optionally protected form of $Ar^1$ and $P^1$ and $P^2$ are each independently either hydrogen or a protecting group provided that the compound of formula (II) contains at least one protecting group.

Optionally protected forms $Ar^{1a}$ of the preferred groups $Ar^1$ may be selected from:

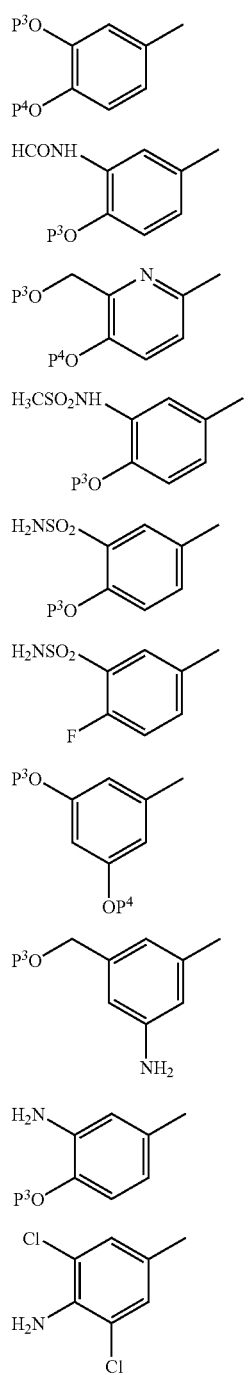

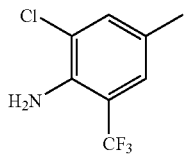

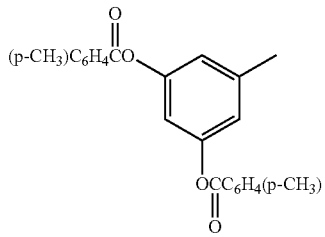

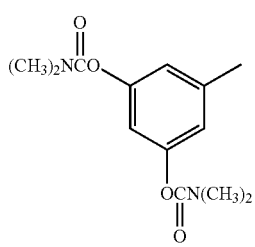

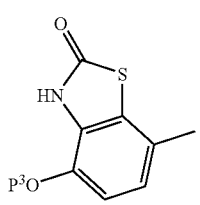

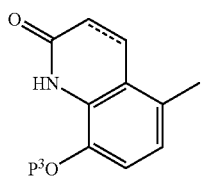

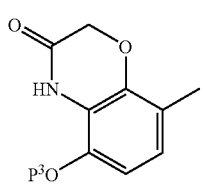

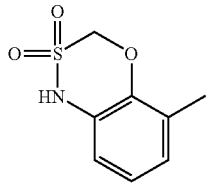

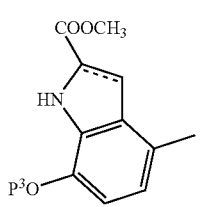

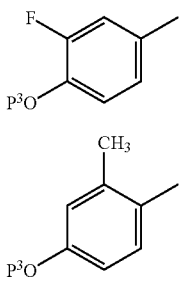

wherein P³ and P⁴ are each independently either hydrogen or a protecting group, and the dotted line in (xva) and (xviii) denotes an optional double bond. It will be appreciated that when Ar¹ represents a group (vi), (x), (xi), (xii) or (xiii) no protection is required for Ar¹.

Suitable protecting groups may be any conventional protecting group such as those described in "Protective Groups in Organic Synthesis" by Theodora W Greene and Peter G M Wuts, 3rd edition (John Wiley & Sons, 1999). Examples of suitable hydroxyl protecting groups represented by $P^2$, $P^3$ and $P^4$ are esters such as acetate ester; aralkyl groups such as benzyl, diphenylmethyl, or triphenylmethyl; silyl groups such as trialkylsilyl-alkoxyalkyl; and tetrahydropyranyl. Examples of suitable amino protecting groups represented by $P^1$ include benzyl, α-methylbenzyl, diphenylmethyl, triphenylmethyl, benzyloxycarbonyl, tert-butoxycarbonyl, and acyl groups such as trichloroacetyl or trifluoroacetyl.

As will be appreciated by the person skilled in the art, use of such protecting groups may include orthogonal protection of groups in the compounds of formula (II) to facilitate the selective removal of one group in the presence of another, thus enabling selective functionalisation of a single amino or hydroxyl function. For example, the —CH(OH) group may be orthogonally protected as CHOP² using, for example, a trialkylsilyl group such as triethylsilyl. A person skilled in the art will also appreciate other orthogonal protection strategies, available by conventional means as described in Theodora W Greene (see above).

The deprotection to yield a compound of formula (I) or (Ia) may be effected using conventional techniques. It will be apparent to persons skilled in the art that the deprotection method employed should not effect cleavage of the —OCR⁶R⁷ moiety.

When P³ and/or P⁴ is tetrahydropyranyl this may be cleaved by hydrolysis under acidic conditions, for example using aqueous acetic acid. Acyl groups represented by P¹ may be removed by hydrolysis, for example with a base such as sodium hydroxide, or a group such as trichloroethoxycarbonyl may be removed by reduction with, for example, zinc and acetic acid. Other deprotection methods may be found in Theodora W Greene (see above).

In a particular embodiment of the above process, when Ar¹ᵃ represents a group (ia) or (iiia) the groups P³O and P⁴O may together represent a protected group:

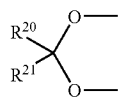

wherein $R^{20}$ and $R^{21}$ are independently selected from hydrogen, $C_{1-6}$alkyl eg. methyl, or aryl eg. phenyl, or together form a carbocyclic ring containing from 3 to 7 carbon atoms.

A suitable precursor group $R^{1a}$, $R^{2a}$, and/or $R^{3a}$ in the compounds of formulae (II) and (III) would be a group which is convertible to the desired group $R^1$, $R^2$, and/or $R^3$, before, after or simultaneously with the removal of the protecting groups $R^{13}$, $R^{14}$, and/or $R^{15}$. For example, $R^{1a}$, $R^{2a}$, and/or $R^{3a}$ may suitably be a protected version of a group $R^1$, $R^2$, and $R^3$ respectively, such that removal of the protecting group gives the desired group $R^1$, $R^2$, or $R^3$. Preferred protecting groups in $R^{1a}$, $R^{2a}$, and/or $R^{3a}$ are those which may be removed under the conditions used for the removal of the protecting groups $P^1$, $P^2$, $P^3$ and/or $P^4$.

The compound of formula (III) may be converted to a compound of formula (I) or (Ia) by hydrolysis with dilute aqueous acid, for example acetic acid or hydrochloric acid in a suitable solvent or by transketalisation in an alcohol, for example ethanol, in the presence of a catalyst such as an acid (for example, toluenesulphonic acid) or a salt (such as pyridinium tosylate) at normal or elevated temperature.

Compounds of formulae (II) and (III) wherein P¹ is hydrogen may be prepared from the corresponding compound of formula (IV):

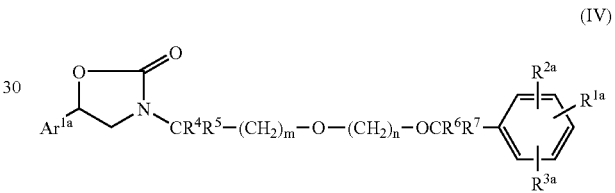

or a salt or solvate thereof, wherein $Ar^{1a}$, $R^4$, $R^5$, $R^6$, $R^7$, m, and n are as defined for the compound of formula (II) or (III) and $R^{1a}$, $R^{2a}$, and $R^{3a}$ are each independently either the same as $R^1$, $R^2$, and $R^3$ respectively as defined for the compound of formula (II) or (III) or a precursor for said group $R^1$, $R^2$, or $R^3$.

A suitable precursor group $R^{1a}$, $R^{2a}$, and/or $R^{3a}$ in the compound of formula (IV) would be a group which is convertible to the desired group $R^1$, $R^2$, and/or $R^3$. Suitably, such conversions are carried out using conventional methods which are known in the art. For example, where $R^1$ is to be —NR⁸SO₂R⁹, a suitable precursor group $R^{1a}$ in the compound of formula (IV) would have the amine —NHR⁸ in place of the substituent $R^1$, such that the desired substituent $R^1$ may be formed by reaction with the appropriate sulphonyl chloride (i.e. R⁹SO₂Cl) before deprotection to form the compound of formula (I).

As a second example, where $R^1$ is to be —NR⁸C(O)NHR⁹, a suitable precursor group $R^{1a}$ in the compound of formula (IV) would have the amine —NHR⁸ in place of the substituent $R^1$, such that the desired substituent $R^1$ may be formed by reaction with the appropriate isocyanate (i.e. R⁹NCO) before deprotection to form the compound of formula (I). Alternatively, where $R^1$ is to be —NHC(O)NHR⁹, a suitable precursor group $R^{1a}$ in the compound of formula (IV) has —NO₂ in place of the substituent $R^1$ which may be reduced to form the corresponding primary amine before reaction with the isocyanate R⁹NCO as described above to form the desired urea substituent $R^1$. The reduction of the —NO₂ group may be effected by any suitable method such as reaction with aluminium amalgam in tetrahydrofuran, or with zinc in ammonium chloride solution.

As a further example, where R¹ is to be —NR⁸C(O)R⁹, a suitable precursor group R¹ᵃ in the compound of formula (IV) would have the amine —NHR⁸ in place of the substituent R¹, such that the desired substituent R¹ may be formed by reaction with the appropriate acyl chloride (i.e. R⁹C(O)Cl) before deprotection to form the compound of formula (I).

As a further example, where R¹ is to be —NR⁸C(O)OR⁹, a suitable precursor group R¹ᵃ in the compound of formula (IV) would have the amine —NHR⁸ in place of the substituent R¹, such that the desired substituent R¹ may be formed by reaction with the appropriate chloroformate (i.e. R⁹OC(O)Cl) before deprotection to form the compound of formula (I).

Alternatively, where R¹ is to be an optionally substituted aryl group, a suitable precursor group R¹ᵃ in the compound of formula (IV) would have a halo substituent, for example iodo, in place of the substituent R¹, such that the desired substituent R¹ may be formed by reaction with bis(pinacolato)diboron followed by reaction with the appropriate optionally substituted haloaryl group, before deprotection to form the compound of formula (I). Alternatively, where R¹ is to be an optionally substituted aryl group, a suitable precursor group R¹ᵃ in the compound of formula (IV) would have a halo substituent, for example iodo, in place of the substituent R¹, such that the desired substituent R¹ may be formed by reaction with the appropriate optionally substituted arylboronic acid, for example an optionally substituted phenylboronic acid, before deprotection to form the compound of formula (I).

Alternatively, R¹ᵃ, R²ᵃ, and/or R³ᵃ may suitably be a protected version of a group R¹, R², and R³ respectively, such that removal of the protecting group gives the desired group R¹, R², or R³. Preferred protecting groups in R¹ᵃ, R²ᵃ, and/or R³ᵃ are those which may be removed under the conditions used for the removal of the protecting groups P³ and P⁴, or the conditions used for the conversion of the compound of formula (IV) to the compound of formulae (II) or (III). For example, an —NH— group in the desired group R¹, R², or R³ may be protected by a 2-(trimethylsilyl)ethoxymethyl group or a tert-butoxycarbonyl group.

The conversion of a compound of formula (IV) to a compound of formula (II) or (III) may be effected by treatment with a base, for example a non-aqueous base, such as potassium trimethylsilanolate, or an aqueous base such as aqueous sodium hydroxide, in a suitable solvent such as tetrahydrofuran.

Compounds of formula (IV) may be prepared according to a first method (a) by coupling the corresponding compound of formula (V):

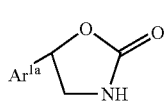

(V)

or a salt or solvate thereof, wherein Ar¹ᵃ is defined for the compound of formula (IV) with a compound of formula (VI):

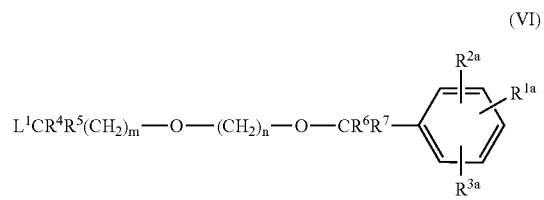

(VI)

wherein R¹ᵃ, R²ᵃ, R³ᵃ, R⁴, R⁵, R⁶, R⁷, m, and n are as defined for the compound of formula (IV) and L¹ is a leaving group, for example a halo group (typically bromo or iodo) or a sulphonate such as an alkyl sulphonate (typically, methanesulphonate), an arylsulphonate (typically, toluenesulphonate), or a haloalkyl sulphonate (typically, trifluoromethanesulphonate).

The coupling of a compound of formula (V) with a compound of formula (VI) may be effected in the presence of a base, such as a metal hydride, for example sodium hydride, an alkoxide such as potassium t-butoxide or an inorganic base such as caesium carbonate, in an aprotic solvent, for example dimethylformamide.

Compounds of formula (VI) may be prepared for example by analogy with the method described in WO 02/066422.

Compounds of formula (VI) may be prepared by coupling a compound of formula (VII):

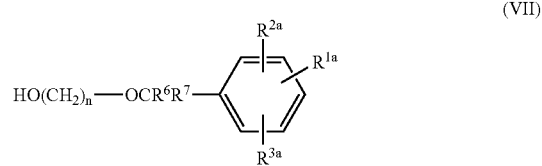

(VII)

wherein R¹ᵃ, R²ᵃ, R³ᵃ, R⁶, R⁷, and n are as defined for the compound of formula (VI), with a compound of formula (VIII):

L²-CR⁴R⁵(CH₂)ₘ-L² (VIII)

wherein R⁴, R⁵, and m are as defined for the compound of formula (VI), and L² is a leaving group such as halo (typically bromo).

The coupling of compounds (VII) and (VIII) may be effected in the presence of a base, such as a metal hydride, for example sodium hydride, or an inorganic base such as caesium carbonate, in an aprotic solvent, for example dimethylformamide. Alternatively, the coupling of compounds (VII) and (VIII) may be effected under phase transfer conditions, suitably in excess aqueous alkali such as 50% aqueous sodium hydroxide, optionally in the presence of a phase transfer catalyst such as a tetrabutylammonium salt, for example tetrabutylammonium bromide.

Compounds of formula (VIII) are commercially available or may be prepared by methods well known to the person skilled in the art.

Compounds of formula (VII) may be prepared by coupling the corresponding compound of formula (IX):

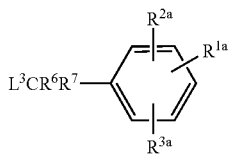
(IX)

wherein $R^{1a}$, $R^{2a}$, $R^{3a}$, $R^6$, and $R^7$ are as defined for the desired compound of formula (VII), and $L^3$ is a leaving group such as halo (typically bromo);

with the dihydroxy compound of formula $HO(CH_2)_nOH$ wherein n is as defined for the compound of formula (VII). The coupling of a compound of formula (XII) with the dihydroxy compound may be effected by methods analogous to those described for the coupling of compounds (VII) and (VIII).

Compounds of formula (IX) are commercially available or may be prepared by methods well known to the person skilled in the art.

According to an alternative process (b), a compound of formula (IV) as defined above may be prepared by coupling the corresponding compound of formula (X):

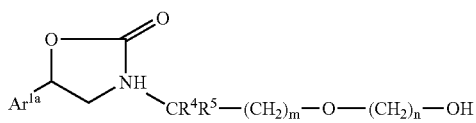
(X)

wherein $Ar^{1a}$, $R^4$, $R^5$, m, and n are as defined for the desired compound of formula (IV), with the corresponding compound of formula (IX) as defined above in which $R^{1a}$, $R^{2a}$, $R^{3a}$, $R^6$, and $R^7$ are as defined for the desired compound of formula (IV) and $L^3$ is a leaving group such as halo (typically bromo). This coupling may be effected by methods analogous to those described for the coupling of compounds (VII) and (VIII).

Compounds of formula (X) may be prepared by coupling the corresponding compound of formula (V) as defined above wherein $R^{13}$ and $R^{14}$ are as defined for the desired compound of formula (XIII) with the corresponding compound of formula (XI):

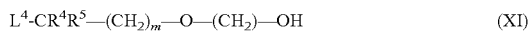
(XI)

or a protected derivative thereof, wherein $R^4$, $R^5$, m and n are as defined for the desired compound of formula (X) and $L^4$ is a leaving group such as halo (typically bromo). The coupling of compounds of formulae (V) and (XI) may be effected by methods analogous to those described for the coupling of compounds of formulae (VII) and (VIII).

Compounds of formula (XI) may be prepared from the corresponding compounds of formula (VIII) as defined above with the dihydroxy compound of formula $HO(CH_2)_nOH$ wherein n is as defined for the desired compound of formula (XI), by methods analogous to those described for the coupling of compounds of formula (VII) and (VIII).

Alternatively, compounds of formula (X) may be prepared by coupling the corresponding compound of formula (XII):

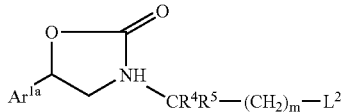
(XII)

wherein $Ar^{1a}$, $R^4$, $R^5$, and m are as defined for the desired compound of formula (X) and $L^2$ is a leaving group such as halo (typically bromo), with the dihydroxy compound of formula $HO(CH_2)_nOH$, wherein n is as defined for the desired compound of formula (X), by methods analogous to those described for the coupling of compounds of formula (VII) and (VIII).

The compound of formula (XII) may be prepared by coupling the corresponding compound of formula (V) as previously defined wherein $Ar^{1a}$ as defined for the desired compound of formula (X), with the corresponding compound of formula (VIII) as previously defined wherein $R^4$, $R^5$, and m are as defined for the desired compound of formula (X) and $L^2$ is a leaving group such as halo (typically bromo).

The coupling of compounds of formulae (V) and (VIII) may be effected by methods analogous to those described for the coupling of compounds of formulae (V) and (VI).

In a further alternative process (c) compounds of formula (IV) as defined above may be prepared by coupling the corresponding compound of formula (XIII):

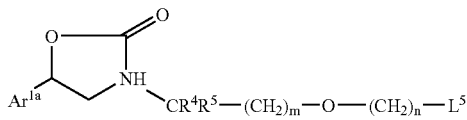
(XIII)

wherein $Ar^{1a}$, $R^4$, $R^5$, m and n are as defined for the compound of formula (IV) and $L^5$ is a leaving group, for example a sulphonate such as an alkyl sulphonate (typically, methanesulphonate), an arylsulphonate (typically, toluenesulphonate), or a haloalkyl sulphonate (typically, trifluoromethanesulphonate), or a halide, eg. bromide, with a compound of formula (XIV):

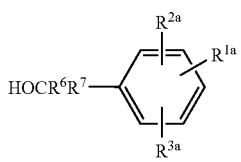
(XIV)

wherein $R^{1a}$, $R^{2a}$, $R^{3a}$, $R^6$, and $R^7$ are as defined for the compound of formula (IV).

The coupling of compounds of formulae (XIII) and (XIV) may be effected by methods analogous to those described for the coupling of compounds of formulae (V) and (VI).

The compound of formula (XIII) may be prepared by converting the hydroxyl group in a compound of formula (X) into a leaving group $L^4$ such as a methansulphonate group using methods known in the art, for example by reaction with methanesulphonyl chloride in the presence of a suitable base, for example $NEt(^1Pr)_2$, in a suitable solvent such as dichloromethane.

The compounds of formula (XIV) are commercially available or may be prepared using methods known in the art.

During the synthesis of the compound of formula (X), appropriate protecting chemistry may be used, for example, the compounds of formula (XI) and the dihydroxy compound of formula HO(CH$_2$)$_n$OH may be protected so as to improve the yield of the desired intermediates. Suitable protecting strategies will be appreciated by the person skilled in the art and may also be found in Theodora W. Greene (see above). Thus, for example, a primary hydroxyl group may be protected with a trialkylsilyl group such as tert-butyldimethylsilyl or with a benzyl group.

In a further process (d) compounds of formula (IV) as defined above may be prepared by coupling a compound of formula (XV):

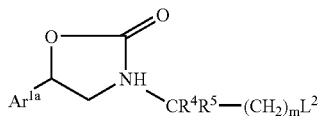

(XV)

wherein Ar$^{1a}$, R$^4$, R$^5$, and m are as defined for formula (IV) and L$^2$ is defined as for formula (VIII), with a compound of formula (VII) as defined above. The reaction of compounds (XV) and (VII) may be effected in a similar manner to the coupling of compounds (VIII) and (VII).

Compounds of formula (XV) may be prepared by reacting a compound of formula (V) with a compound of formula (VIII) in a similar manner to the reaction of compounds (V) and (XI).

In a further general process (B) a compound of formula (I) may be obtained by alkylation of an amine of formula (XVI):

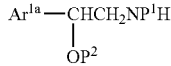

(XVI)

wherein Ar$^{1a}$, P$^1$ and P$^2$ are as hereinbefore defined, for compounds for formula (II); with a compound of formula (VI):

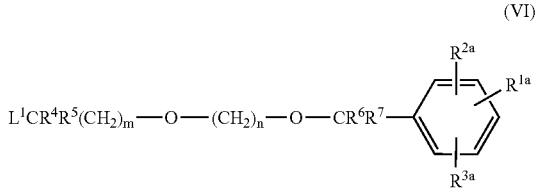

(VI)

wherein R$^4$, R$^5$, R$^6$, R$^7$, R$^{1a}$, R$^{2a}$, R$^{3a}$, m and n are as defined for compounds of formula (II) and L$^1$ represents a leaving group such as halo (typically bromo), followed by removal of any protecting groups present by conventional methods as described above for the deprotection of compounds of formula (II).

The reaction of compounds of formulae (XVI) and (VI) may be optionally effected in the presence of an organic base, such as a trialkylamine, for example diisopropyl ethylamine, and in a suitable solvent, for example dimethylformamide.

Compounds of formula (XVI) are known in the art, for example EP-A-0947498, or may readily be prepared by a person skilled in the art, using known methods, for example as described in WO 02/070490.

Further details concerning preparation of compounds (XVI) wherein Ar$^1$ is a group (ii) and (iv) can be found in GB2162842; concerning the preparation of compounds (XVI) wherein Ar$^1$ is a group (i), (vii), and (xv) in EP-A-162576; concerning the preparation of compounds (XVI) wherein Ar$^1$ is a group (iii) in EP-A-220054; concerning the preparation of compounds (XVI) wherein Ar$^1$ is a group (x) in GB2165542 and concerning the preparation of compounds (XVI) wherein Ar$^1$ is a group (c) in GB2230523.

In a yet further general process (C), a compound of formula (I) may be prepared by reacting an amine of formula (XVI) as defined hereinabove, with a compound of formula (XVII):

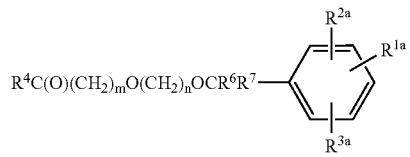

(XVII)

wherein R$^4$, R$^6$, R$^7$, R$^{1a}$, R$^{2a}$, R$^{3a}$, m and n are as hereinbefore defined;

under conditions suitable to effect reductive amination, for example in the presence of a reducing agent such as borohydride, typically tetramethylammonium (triacetoxy) borohydride.

A compound of formula (XVII) may be prepared by methods known in the art, for example from a compound of formula (VI) as defined hereinabove via Kornblum oxidation.

It will be appreciated that in any of the general processes (A), (B) or (C) as well as the processes for (a) to (d) for preparing compounds (IV) described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly. It will also be appreciated that in general processes (B) and (C) appropriate protecting groups may be employed if necessary and/or desired and removed at any suitable stage of the synthesis, eg. in the last stage, as described in general process (A).

The enantiomeric compounds of the invention may be obtained (i) by separation of the components of the corresponding racemic mixture, for example, by means of a chiral chromatography column, enzymic resolution methods, or preparing and separating suitable diastereoisomers, or (ii) by direct synthesis from the appropriate chiral intermediates by the methods described herein.

Optional conversion of a compound of formula (I) or (Ia) to a corresponding salt may conveniently be effected by reaction with the appropriate acid or base. Optional conversion of a compound of formula (I) or (Ia) to a corresponding solvate or physiologically functional derivative may be effected by methods known to those skilled in the art.

According to a further aspect, the present invention provides novel intermediates for the preparation of compounds of formula (I) or (Ia), for example compounds of formula (II) (III) and (IV) as defined above, or an optical isomer, a salt, or a protected derivative thereof; and compounds of formula (X) as defined above, or an optical isomer, a salt, or a protected derivative thereof.

For a better understanding of the invention, the following Examples are given by way of illustration.

SYNTHETIC EXAMPLES

Throughout the examples, the following abbreviations are used:

LCMS: Liquid Chromatography Mass Spectrometry
MS: mass spectrum
TSP+ve: thermospray mass spectrum positive mode
SPE: solid phase extraction
RT: retention time
DMF: N,N-dimethylformamide
DCM: dichloromethane
EtOAc: ethyl acetate
EtOH: ethanol
MeOH: methanol
HPLC: high performance liquid chromatography
TLC: thin layer chromatography
Sat: saturated
bp: boiling point
ca: circa
h: hour(s)
min: minute(s)
d: doublet
dd: double doublet
s: singlet
brs: broad singlet
All temperatures are given in degrees centigrade.
Ammonia refers to 0.880 (aqueous) ammonia.
Silica gel refers to Merck silica gel 60 Art number 7734.
Flash silica gel refers to Merck silica gel 60 Art number 9385.
Biotage refers to prepacked silica gel cartridges containing KP-Sil run on flash 12i chromatography module.
Bond Elut are prepacked cartridges used in parallel purifications, normally under vacuum. These are commercially available from Varian.
SCX refers to prepacked SPE cartridges containing benzenesulphonic acid ion exchange resin.
Preparative thin layer chromatography was carried out on silica gel, 20×20 cm, Whatman PK6F, 60A, 1 mm thick.
LC was conducted on a Luna 3 μm C18(2) column (50 mm×2 mm id) eluting with 0.05% v/v trifluoroacetic acid in water (solvent A) and 0.05% v/v trifluoroacetic acid in acetonitrile (solvent B) using the elution gradient 0-8.0 min 0% B-95% B, 8.0-8.01 min 95% B-0% B, with a flow rate of 1 mL/min with a column temperature of 40° C.
LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 100% B, 5.3-5.5 min 0% B at a flow rate of 3 ml/min. The mass spectra were recorded on a Fisons VG Platform spectrometer using electrospray positive and negative mode (ES+ve and ES-ve).
HPLC was conducted using the same chromatographic system as for the LCMS.

Example 1

(1R)-1-(4-Amino-3,5-dichlorophenyl)-2-[(6-{2-[(2,6-dichlorobenzyl)oxy]ethoxy}hexyl)amino]ethanol acetate i) 2-(2,6-Dichlorobenzyloxy)ethanol Sodium methoxide (104.4 g, 1.93 mol) was added portionwise to ethylene glycol (3.74 L) under $N_2$, keeping the temperature below 35° C. After 1-2 h, 2,6-dichlorobenzylbromide (400 g, 1.67 mol) was added and the mixture heated to 55-60° C. for 1 h. On cooling to 20° C. water (2.14 L) was added and the mixture extracted with ethyl acetate (2.14 L). The aqueous layer was separated and extracted twice with ethyl acetate (2.14 L, 1.28 L). The combined organic extracts were washed with water (2.14 L) then evaporated to dryness to afford a colourless oil (371.8 g)-LC RT=4 min. This may be chromatographed on silica (Biotage) eluting with 10% ethyl acetate in 60/80 petrol to afford the title compound.

$^1H$ NMR (500 MHz, $CDCl_3$) δ 7.33 (d, 2H, J=8.2 Hz), 7.20 (t, 1H, J=8.2 Hz), 4.83 (s, 2H), 3.75 (m, 2H), 3.68 (m, 2H), 2.18 (t, 1H, J=6.3 Hz)

ii) 2-({2-[(6-Bromohexyl)oxy]ethoxy}methyl)-1,3-dichlorobenzene

50% aq NaOH (1.89 L), 2-(2,6-dichlorobenzyloxy)ethanol (473.2 g), 1,6-dibromohexane (2.44 kg, 5 eq) and tetrabutylammonium bromide (34.1 g, 5 mol %) in toluene (1.89 L) was heated to 55-60° C. for 8-20 h. On cooling water (558 mL) and toluene (558 mL) were added. The aqueous phase was separated and diluted with water (1 L) then back extracted with toluene (1.1 L). The combined toluene extracts were washed twice with water (2.2 L), then evaporated to dryness on a rotary evaporator. The excess 1,6-dibromohexane was removed using a wiped film evaporator, and the resulting crude product chromatographed on silica (5 kg Biotage), eluting with 5% ethyl acetate in petrol 60/80, to give the title compound (503.2 g)-LC RT=7.0 min.

iii) (1R)-1-(4-Amino-3,5-dichlorophenyl)-2-[(6-{2-[(2,6-dichlorobenzyl)oxy]ethoxy}hexyl)amino]ethanol acetate A mixture of (1R)-2-amino-1-(4-amino-3,5-dichlorophenyl)ethanol (EP460924) (177 mg) and 2-({2-[(6-bromohexyl)oxy]ethoxy}methyl)-1,3-dichlorobenzene (153 mg) in dimethylformamide (1 ml) and diisopropylethylamine (0.2 ml) was stirred at 20° C. for 20 h. The mixture was concentrated under reduced pressure and the residue was partitioned between ethyl acetate and water. The organic phase was washed with water, brine, dried and evaporated to dryness. The residue was purified by chromatography on a silica SPE cartridge eluting with 10% aqueous ammonia in ethanol-dichloromethane (1:19). Appropriate fractions were combined and concentrated and then diluted in acetic acid and ethanol. The solution was then evaporated to give the title compound (177 mg) LCMS RT=2.76 min, ES+ve m/z 523/525/527 $(M+H)^+$

Example 2

6-{2-[(6-{2-[(2,6-Dichlorobenzyl)oxy]ethoxy}hexyl)amino]-1-hydroxyethyl}-2-(hydroxymethyl)pyridin-3-ol A mixture of 2-amino-1-(2-phenyl-4H-[1,3]dioxino[5,4-b]pyridin-6-yl)ethanol (EP220054A2) (93 mg) and 2-({2-[(6-bromohexyl)oxy]ethoxy}methyl)-1,3-dichlorobenzene (98 mg) in dimethylformamide (1 ml) and diisopropylethylamine (0.2 ml) was heated to 70° C. for 4 h and then at 20° C. for 16 h. The mixture was concentrated under reduced pressure and the residue was partitioned between ethyl acetate and water. The organic phase was washed with water, brine, dried and evaporated to dryness. The residue was dissolved in ethanol and applied to an SCX-2 cartridge (10 g) eluting with ethanol, followed by 10% aqueous ammonia in ethanol. The ammoniacal fractions were concentrated under reduced pressure, and the residue was dissolved in acetic acid (5 ml) and water (2 ml) and the mixture was heated to 70° C. for 40 min. The solvent was removed under reduced pressure and the residue was purified by chromatography on a silica SPE cartridge (10 g) eluting with 10% aqueous ammonia in ethanol-dichloromethane (1:9 to 1:3). Appropriate fractions were combined and concentrated and the residue dissolved in acetic acid and re-evaporated to dryness to give the title compound (124 mg). LCMS RT=2.46 min, ES+ve m/z 487/489/491 (M+H)$^+$.

Example 3

4-{(1R)-2-[(6-{2-[(2,6-Dichlorobenzyl)oxy]ethoxy}hexyl)amino]-1-hydroxyethyl}-2-fluorophenol formate This was prepared similarly to example 1 iii) from 4-[(1R)-2-amino-1-hydroxyethyl]-2-fluorophenol LCMS RT=2.58 min ES+ve m/z 474/476 (M+H$^+$)

Example 4

N-(5-{(1R)-2-[(6-{2-[(2,6-Dichlorobenzyl)oxy]ethoxy}hexyl)amino]-1-hydroxyethyl}-2-hydroxyphenyl)methanesulfonamide formate This was prepared similarly to example 1 iii) from N-{5-[(1R)-2-amino-1-hydroxyethyl]-2-hydroxyphenyl}methanesulfonamide LCMS RT=2.56 min ES+ve m/z 549/551 (M+H$^+$)

Example 5

5-[(1R)-2-({6-[(2-{[(2,6-Dichlorophenyl)methyl]oxy}ethyl)oxy]hexyl}amino)-1-hydroxyethyl]-2-hydroxyphenyl}formamide formate i) {5-{(1R)-2-[Bis(phenylmethyl)amino]-1-hydroxyethyl}-2-[(phenylmethyl)oxy]phenyl}formamide A mixture of {5-[(2R)-2-oxiranyl]-2-[(phenylmethyl)oxy]phenyl}formamide (WO 0276933) (200 mg) and dibenzylamine (0.75 ml) were heated in a microwave oven at 150° for 30 min. The mixture was allowed to cool to 20° and was purified on a silica SPE bond elut cartridge (10 g) using a gradient of 0% to 50% EtOAc in cyclohexane (Gradmaster™). The appropriate fractions were evaporated in vacuo and the residue further purified by mass-directed autopreparative HPLC to give the title compound (123 mg). LCMS RT=2.75 min.

ii) (5-{(1R)-2-[Bis(phenylmethyl)amino]-1-hydroxyethyl}-2-hydroxyphenyl)formamide A solution of {5-{(1R)-2-[bis(phenylmethyl)amino]-1-hydroxyethyl}-2-[(phenylmethyl)oxy]phenyl}formamide (1.40 g) in EtOAc (15 ml) and EtOH (15 ml) was hydrogenated over 10% palladium on carbon (140 mg). When hydrogen uptake had ceased the mixture was filtered through celite, the solvent evaporated in vacuo and the residue purified on a silica SPE bond elut cartridge (70 g) using a gradient of 0% to 5% MeOH in DCM (Gradmaster™). The appropriate fractions were evaporated in vacuo to give the title compound (380 mg). LCMS RT=2.17 min.

iii) {5-{(1R)-2-[Bis(phenylmethyl)amino]-1-hydroxyethyl}-2-[({[2-(trimethylsilyl)ethyl]oxy}methyl)oxy]phenyl}formamide A solution of (5-{(1R)$_2$-[bis(phenylmethyl)amino]-1-hydroxyethyl}-2-hydroxyphenyl)formamide (354 mg) in DMF (10 ml) under nitrogen was treated with sodium hydride (60% dispersion in mineral oil, 38 mg) and the mixture stirred at 20° for 10 min. 2-(Trimethylsilyl)ethoxymethyl chloride (0.17 ml) was added and the mixture was stirred at 20° for 3 h. Phosphate buffer solution (pH 6.5) and water were added and the mixture was extracted with EtOAc. The extract was washed with water and dried (Na$_2$SO$_4$). Solvent evaporation in vacuo gave a residue which was purified on a silica SPE bond elut cartridge (20 g) using a gradient of 0% to 2% MeOH in DCM (Gradmaster™). The appropriate fractions were evaporated in vacuo to give the title compound (286 mg). LCMS RT=3.08 min.

iv) {5-[(1R)-2-Amino-1-hydroxyethyl]-2-[({[2-(trimethylsilyl)ethyl]oxy}methyl)oxy]phenyl}formamide A solution of {5[(1R)-2-[bis(phenylmethyl)amino]-1-hydroxyethyl}-2-[({[2-(trimethylsilyl)ethyl]oxy}methyl)oxy]phenyl}formamide (90 mg) in EtOAc (8 ml) and EtOH (8 ml) was hydrogenated over 10% palladium on carbon (40 mg) and 20% palladium hydroxide on carbon (20 mg). When hydrogen uptake had ceased the mixture was filtered through celite and the solvent evaporated in vacuo to give the title compound (52 mg). LCMS RT=2.31 min.

v) 5-[(1R)-2-({6-[(2-{[(2,6-Dichlorophenyl)methyl]oxy}ethyl)oxy]hexyl}amino)-1-hydroxyethyl]-2-hydroxyphenyl}formamide formate A solution of {5-[(1R)-2-amino-1-hydroxyethyl]-2-[({[2-(trimethylsilyl)ethyl]oxy}methyl)oxy]phenyl}formamide (70 mg), 2-[({2-[(6-bromohexyl)oxy]ethyl}oxy)methyl]-1,3-dichlorobenzene (WO 0324439) (69 mg) and diisopropylethylamine (0.05 ml) in DMF (1 ml) under nitrogen was heated to 50° for 18 h. The mixture was cooled to 20° and the solvent was evaporated in vacuo. The residue was dissolved in acetic acid (2 ml) and water (1 ml) and the mixture was heated to 70° for 3 h. The mixture was cooled to 20° and the solvent was evaporated in vacuo. The residue was purified by mass-directed autopreparative HPLC to give the title compound (23 mg). LCMS RT=2.51 min, ES+ve 499, 501, 503 (MH)$^+$.

Biological Activity

Potency of compounds of the invention at the human beta 2, 1 and 3 receptors was determined using Chinese hamster ovary cells co-expressing the human receptor with a reporter gene. Studies were performed using either whole cells or membranes derived from those cells.

The three beta-receptors are coupled via the Gs G-protein to cause a stimulation of adenylate cyclase resulting in increased levels of cAMP in the cell. For direct cAMP measurements either membranes or cells have been used with either the HitHunter enzyme fragment complementation kit (DiscoveRx) to quantify the levels of cAMP present. These assays provide a measure of agonist potency and intrinsic activity of the compounds at the various receptors.

The reporter gene in the cells has also been used to quantify potency at the beta 1 and 3 receptors. This is a reporter of cAMP levels using the cAMP response element upstream of a firefly luciferase gene. After stimulation of the receptor with an agonist an increase in the level of luciferase is measured as a quantification of the level of cAMP in the cell.

In this assay the potency of compounds at the human beta-2 receptor is expressed as a $pEC_{50}$ value. Compound of Examples 1 to 5 had a $pEC_{50}$ of >6.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. A compound of formula (I)

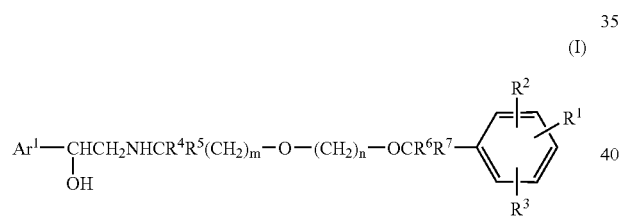

or a salt thereof, wherein:
m is an integer of from 2 to 8;
n is an integer of from 2 to 5;
with the proviso that m+n is 4 to 10;
$R^1$ is selected from hydrogen, $C_{1-6}$alkyl, hydroxy, halo, $C_{1-6}$haloalkyl, —CN, —XC(O)NR$^9$R$^{10}$, —XNR$^8$C(O)R$^9$, —XNR$^8$C(O)NR$^9$R$^{10}$, —XNR$^8$SO$_2$R$^9$, —XSO$_2$NR$^9$R$^{10}$, XNR$^8$SO$_2$NR$^9$R$^{10}$, —XNR$^9$R$^{10}$, XN$^+$R$^8$R$^9$R$^{10}$, —XNR$^8$C(O)OR$^9$, —XCO$_2$R$^9$, —XNR$^8$C(O)NR$^8$C(O)NR$^9$R$^{10}$, —XSR$^9$, XSOR$^9$, and —XSO$_2$R$^9$;
or $R^1$ is selected from —X-aryl, —X-hetaryl, and —X-(aryloxy), each optionally substituted by 1 or 2 groups independently selected from hydroxy, $C_{1-6}$alkoxy, halo, $C_{1-6}$alkyl, $C_{1-6}$haloalkyl, —NHC(O)(C$_{1-6}$alkyl), —SO$_2$(C$_{1-6}$alkyl), —SO$_2$(aryl), —SO$_2$NH$_2$, —SO$_2$NH(C$_{1-6}$alkyl), —SO$_2$NH(C$_{3-7}$cycloalkyl), —CO$_2$H, —CO$_2$(C$_{1-6}$alkyl), —SO$_2$NH(C$_{3-7}$cycloalkylC$_{1-6}$alkyl), —NH$_2$, —NH(C$_{1-6}$alkyl), or hetaryl optionally substituted by 1 or 2 groups independently selected from hydroxy, $C_{1-6}$alkoxy, halo, $C_{1-6}$alkyl, or $C_{1-6}$haloalkyl;
X is —(CH$_2$)$_p$— or $C_{2-6}$ alkenylene;
p is an integer from 0 to 6;

$R^8$ and $R^9$ are independently selected from hydrogen, $C_{1-6}$alkyl, $C_{3-7}$cycloalkyl, aryl, hetaryl, hetaryl(C$_{1-6}$alkyl)- and aryl(C$_{1-6}$alkyl)- and $R^8$ and $R^9$ are each independently optionally substituted by 1 or 2 groups independently selected from halo, $C_{1-6}$alkyl, $C_{1-6}$haloalkyl, —NHC(O)(C$_{1-6}$alkyl), —SO$_2$(C$_{1-6}$alkyl), —SO$_2$(aryl), —CO$_2$H, —CO$_2$(C$_{1-4}$alkyl), —NH$_2$, —NH(C$_{1-6}$alkyl), aryl(C$_{1-6}$alkyl)-, aryl(C$_{2-6}$alkenyl)-, aryl(C$_{2-6}$alkynyl)-, hetaryl(C$_{1-6}$alkyl)-, —NHSO$_2$aryl, —NH(hetarylC$_{1-6}$alkyl), —NHSO$_2$hetaryl, —NHSO$_2$(C$_{1-6}$alkyl), —NHC(O)aryl, or —NHC(O)hetaryl:

or when $R^1$ is —XNR$^8$C(O)NR$^9$R$^{10}$, $R^8$ and $R^9$ may, together with the —NC(O)N— portion of the group $R^1$ to which they are bonded, form a saturated or unsaturated ring;

or where $R^1$ is —XNR$^8$C(O)OR$^9$, $R^8$ and $R^9$ may, together with the —NC(O)O— portion of the group $R^1$ to which they are bonded, form a saturated or unsaturated ring;

$R^{10}$ is selected from hydrogen, $C_{1-6}$alkyl, $C_{3-7}$cycloalkyl, aryl, hetaryl, hetaryl(C$_{1-6}$alkyl)- and aryl(C$_{1-6}$alkyl)-, or $R^9$ and $R^{10}$, together with the nitrogen to which they are bonded, form a 5-, 6-, or 7- membered nitrogen containing ring;

and $R^9$ and $R^{10}$ are each optionally substituted by one or two groups independently selected from halo, $C_{1-6}$alkyl, and $C_{1-6}$haloalkyl;

$R^2$ is selected from hydrogen, hydroxy, $C_{1-6}$alkyl, $C_{1-6}$alkoxy, halo, aryl, aryl(C$_{1-6}$alkyl)-, $C_{1-6}$haloalkoxy, and $C_{1-6}$ haloalkyl;

$R^3$ is selected from hydrogen, hydroxy, $C_{1-6}$alkyl, $C_{1-6}$alkoxy, halo, aryl, aryl(C$_{1-6}$alkyl)-, $C_{1-6}$haloalkoxy, and $C_{1-6}$haloalkyl;

$R^4$ and $R^5$ are independently selected from hydrogen and $C_{1-4}$ alkyl with the proviso that the total number of carbon atoms in $R^4$ and $R^5$ is not more than 4;

$R^6$ and $R^7$ are independently selected from hydrogen and $C_{1-4}$alkyl with the proviso that the total number of carbon atoms in $R^6$ and $R^7$ is not more than 4, and $Ar^1$ is a group selected from

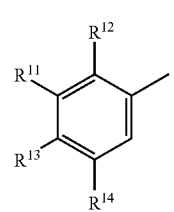

(a)

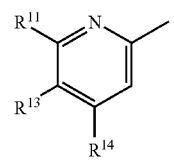

(b)

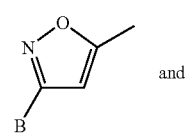

(c)

and

-continued

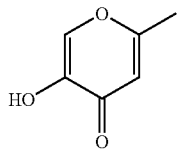
(d)

wherein R¹¹ represents hydrogen, halogen, —(CH$_2$)$_q$OR¹⁵, —NR¹⁵C(O)R¹⁶, —NR¹⁵SO$_2$R¹⁶, —SO$_2$NR¹⁵R¹⁶, —NR¹⁵R¹⁶, —OC(O)R¹⁷ or OC(O)NR¹⁵R¹⁶, and R¹² represents hydrogen, halogen or C$_{1-4}$ alkyl;

or R¹¹ and R¹² together with the benzene ring atoms to which they are attached form a 5- or 6- membered heterocyclic ring;

R¹³ represents hydrogen, halogen, —OR¹⁵ or —NR¹⁵R¹⁶;

R¹⁴ represents hydrogen, halogen, haloC$_{1-4}$ alkyl, —OR¹⁵, —NR¹⁵R¹⁶, —OC(O)R¹⁷ or OC(O)NR¹⁵R¹⁶;

R¹⁵ and R¹⁶ each independently represents hydrogen or C$_{1-4}$ alkyl, or in the groups —NR¹⁵R¹⁶, —SO$_2$NR¹⁵R¹⁶ and —OC(O)NR¹⁵R¹⁶, R¹⁵ and R¹⁶ independently represent hydrogen or C$_{1-4}$ alkyl or together with the nitrogen atom to which they are attached form a 5-, 6- or 7- membered nitrogen-containing ring, R¹⁷ represents an aryl group which may be unsubstituted or substituted by one or more substituents selected from halogen, C$_{1-4}$ alkyl, hydroxy, C$_{1-4}$ alkoxy or halo C$_{1-4}$ alkyl; and q is zero or an integer from 1 to 4, provided that in the group (a) when R¹¹ represents —(CH$_2$)$_q$OR¹⁵ and q is 1, R¹³ is not OH.

2. A compound of formula (I) according to claim 1 or a salt thereof wherein Ar¹ is selected from the following groups (i) to (xx):

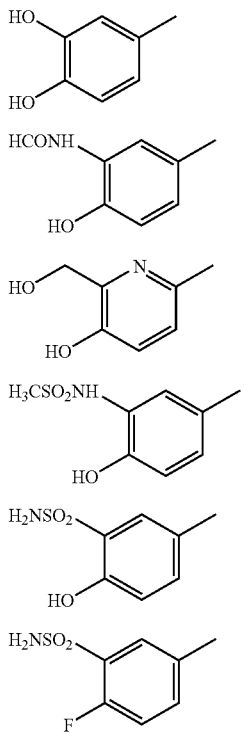

(i)

(ii)

(iii)

(iv)

(v)

(vi)

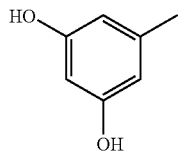
(vii)

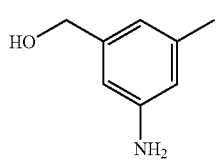
(viii)

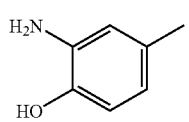
(ix)

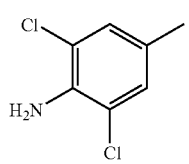
(x)

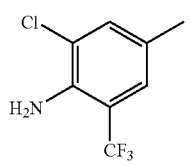
(xi)

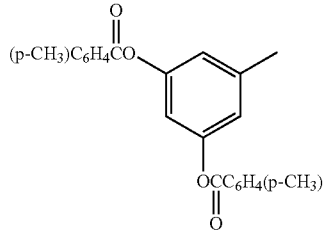
(xii)

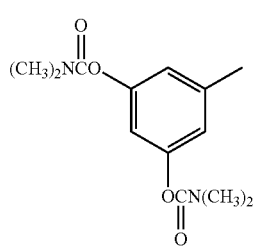
(xiii)

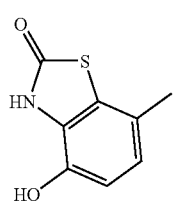
(xiv)

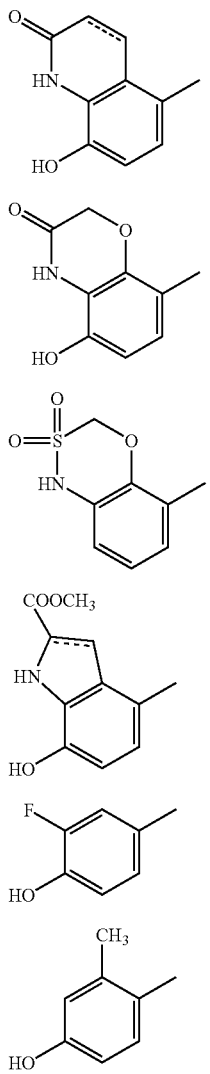

wherein the dotted line in (xv) and (xviii) denotes an optional double bond.

3. A compound of formula (I) according to claim 1 or a salt thereof wherein $R^1$ is selected from hydrogen, $C_{1-4}$alkyl, hydroxy, halo, —$NR^8C(O)NR^9R^{10}$, and —$NR^8SO_2R^9$, wherein $R^8$ is hydrogen and $R^9$ is selected from hydrogen, $C_{1-6}$alkyl, $C_{3-6}$cycloalkyl, and aryl and is optionally substituted as defined in claim 1.

4. A compound of formula (I) or a salt thereof according to claim 1, wherein $R^2$ and $R^3$ are independently selected from hydrogen, halogen, halo$C_{1-6}$alkyl, $C_{1-6}$alkyl and phenyl or substituted phenyl.

5. A compound of formula (I) or a salt thereof according to claim 1, wherein $R^1$ represents a substituent other than hydrogen, and $R^2$ and $R^3$ each represent hydrogen.

6. A compound of formula (I) or a salt thereof according to claim 1, wherein $R^1$ represents hydrogen and $R^2$ and $R^3$ each represent a substituent as defined above, at least one of which is other than hydrogen, and $R^2$ and $R^3$ are each independently attached to the ortho- or meta-positions relative to the —$OCR^6R^7$-link.

7. A compound of formula (I) or a salt thereof according to claim 1, wherein $R^4$ and $R^5$ are independently selected from hydrogen and methyl.

8. A compound of formula (I) or a salt thereof according to claim 1, wherein $R^6$ and $R^7$ are independently selected from hydrogen and methyl.

9. A compound of formula (I) or a salt thereof according to claim 1 wherein m is 4, 5 or 6, and n is 2 or 3.

10. A compound of formula (I) according to claim 1 selected from the group consisting of:
   (1R)-1-(4-amino-3,5-dichlorophenyl)-2-[(6-{2-[(2,6-dichlorobenzyl)oxy]ethoxy}hexyl)amino]ethanol;
   6-{2-[(6-{2-[(2,6-dichlorobenzyl)oxy]ethoxy}hexyl)amino]-1-hydroxyethyl}-2-(hydroxymethyl)pyridin-3-ol;
   4-{(1R)-2-[(6-{2-[(2,6-dichlorobenzyl)oxy]ethoxy}hexyl)amino]-1-hydroxyethyl}-2-fluorophenol;
   N-(5-{(1R)-2-[(6-{2-[(2,6-dichlorobenzyl)oxy]ethoxy}hexyl)amino]-1-hydroxyethyl}-2-hydroxyphenyl)methanesulfonamide;
   5-[(1R)-2-({6-[(2-{[(2,6-dichlorophenyl)methyl]oxy}ethyl)oxy]hexyl}amino)-1-hydroxyethyl]-2-hydroxyphenyl}formamide formate
or a salt thereof.

11. A compound of formula (I) or a salt thereof according to claim 1, wherein p is an integer ranging from 0 to 4.

12. A compound of formula (I) or a salt thereof according to claim 1, wherein $R^8$ and $R^9$, together with the NC(O)N— portion of the group $R^1$ to which they are bonded, form a 5-, 6- or 7-membered ring.

13. A compound of formula (I) or a salt thereof according to claim 12, wherein the 5-, 6- or 7-membered ring is an imidazolidine ring.

14. A compound of formula (I) or a salt thereof according to claim 13, wherein the imidazolidine ring is imidazolidine-2,4-dione.

15. A compound of formula (I) or a salt thereof according to claim 12, wherein the 5-, 6- or 7-membered ring is a pyrimidine ring.

16. A compound of formula (I) or a salt thereof according to claim 15, wherein the pyrimidine ring is pyrimidine-2,4-dione.

17. A compound of formula (I) or a salt thereof according to claim 1, wherein $R^8$ and $R^9$, together with the NC(O)O— portion of the group $R^1$ to which they are bonded, form a 5-, 6- or 7-membered ring.

18. A compound of formula (I) or a salt thereof according to claim 17, wherein the 5-, 6- or 7-membered ring is an oxazoline ring.

19. A compound of formula (I) or a salt thereof according to claim 18, wherein the oxazoline ring is oxazolidine-2,4-dione.

20. A pharmaceutical formulation comprising a compound of formula (I) according to claim 1 or a pharmaceutically acceptable salt thereof, and a pharmaceutically acceptable carrier or excipient, and optionally one or more other therapeutic ingredients.

21. A combination comprising a compound of formula (I) according to claim 1 or a pharmaceutically acceptable salt thereof, and one or more other therapeutic ingredients.

22. A combination according to claim 21 wherein the one or more therapeutic ingredients is a PDE4 inhibitor, a corticosteroid or an anti-cholinergic agent.

23. A combination according to claim 21 wherein the one or more therapeutic ingredients is 6α,9α-difluoro-17α-[(2- furanylcarbonyl)oxy]-11β-hydroxy-16α-methyl-3-oxo-androsta-1,4-diene-17β-carbothioic acid S-fluoromethyl ester.

24. A process for preparing a compound of formula (I) as defined in claim 1 which comprises:
deprotecting a protected intermediate of formula (II):

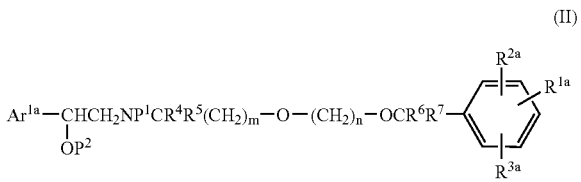

or a salt thereof, wherein $R^4$, $R^5$, $R^6$, $R^7$, m, and n are as defined for the compound of formula (I), and $R^{1a}$, $R^{2a}$, and $R^{3a}$ are each independently either the same as $R^1$, $R^2$, and $R^3$ respectively as defined for the compound of formulae (I) or a precursor for said group $R^1$, $R^2$, or $R^3$, $Ar^{1a}$ represents an optionally protected form of $Ar^1$ and $P^1$ and $P^2$ are each independently either hydrogen or a protecting group provided that the compound of formula (II) contains at least one protecting group;
wherein said process is optionally followed by one or more of the following steps in any order selected from the group consisting of:
(i) removing any protecting groups;
(ii) separating an enantiomer or diastereoisomer from a mixture of enantiomers or diastereoisomers;
(iii) converting the product to a corresponding salt thereof; and
(iv) converting a group $R^{1a}$, $R^{2a}$ and/or $R^{3a}$ to a group $R^1$, $R^2$ and/or $R^3$ respectively.

25. A process for preparing a compound of formula (I) as defined in claim 1 which comprises:
alkylating an amine of formula (XVI):

wherein $Ar^{1a}$ represents an optionally protected form of $Ar^1$ and $P^1$ and $P^2$ are each independently either hydrogen or a protecting group with a compound of formula (VI)

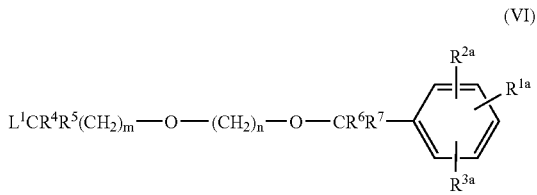

wherein $R^4$, $R^5$, $R^6$, $R^7$, m, and n are as defined for the compound of formula (I), and $R^{1a}$, $R^{2a}$, and $R^{3a}$ are each independently either the same as $R^1$, $R^2$, and $R^3$ respectively as defined for the compound of formula (I), and $L^1$ is a leaving group,
wherein said process is optionally followed by one or more of the following steps in any order selected from the group consisting of:
(i) removing any protecting groups;
(ii) separating an enantiomer or diastereoisomer from a mixture of enantiomers or diastereoisomers;
(iii) converting the product to a corresponding salt thereof; and
(iv) converting a group $R^{1a}$, $R^{2a}$ and/or $R^{3a}$ to a group $R^1$, $R^2$ and/or $R^3$ respectively.

26. A process for preparing a compound of formula (I) as defined in claim 1 which comprises:
reacting an amine of formula (XVI):

wherein $Ar^{1a}$ represents an optionally protected form of $Ar^1$ and $P^1$ and $P^2$ are each independently either hydrogen or a protecting group, with a compound of formula (XVII):

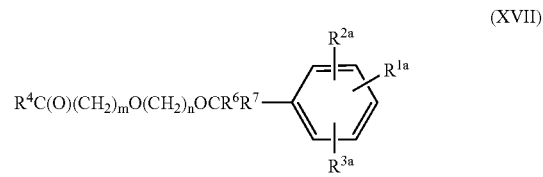

wherein $R^4$, $R^6$, $R^7$, $R^{1a}$, $R^{2a}$, $R^{3a}$, m and n are as hereinbefore defined; under conditions suitable to effect reductive amination,
wherein said process is optionally followed by one or more of the following steps in any order selected from the group consisting of:
(i) removing any protecting groups;
(ii) separating an enantiomer or diastereoisomer from a mixture of enantiomers or diastereoisomers;
(iii) converting the product to a corresponding salt thereof; and
(iv) converting a group $R^{1a}$, $R^{2a}$ and/or $R^{3a}$ to a group $R^1$, $R^2$ and/or $R^3$ respectively.

27. A process according to claim 25, wherein $L^1$ is selected from the group consisting of a halo group and a sulphonate.

28. A process according claim 27, wherein $L^1$ is a sulphonate selected from the group consisting of an alkyl sulphonate, an arylsulphonate, and a haloalkyl sulphonate.

29. A process according to claim 28, wherein the sulphonate is an alkyl sulphonate.

30. A process according to claim 29, wherein the alkyl sulphonate is methanesulphonate.

31. A process according to claim 28, wherein the sulphonate is an arylsulphonate.

32. A process according to claim 31, wherein the arylsulphonate is toluenesulphonate.

33. A process according to claim 28, wherein the sulphonate is a haloalkyl sulphonate.

34. A process according to claim 33, wherein the haloalkyl is trifluoromethanesulphonate.

35. A process according to claim 27, wherein $L^1$ is a halo group.

36. A process according to claim 35, wherein the halo group is a bromo or an iodo group.

* * * * *